(12) United States Patent
Guo

(10) Patent No.: US 11,540,584 B2
(45) Date of Patent: Jan. 3, 2023

(54) INTELLIGENT HAIR GROWTH HELMET

(71) Applicant: Jinxia Guo, Xianyou (CN)

(72) Inventor: Jinxia Guo, Xianyou (CN)

(*) Notice: Subject to any disclaimer, the term of this patent is extended or adjusted under 35 U.S.C. 154(b) by 0 days.

(21) Appl. No.: 17/565,467

(22) Filed: Dec. 30, 2021

(65) Prior Publication Data
US 2022/0117346 A1 Apr. 21, 2022

(51) Int. Cl.
*A42B 3/14* (2006.01)
*A61N 5/067* (2006.01)
*A61N 5/06* (2006.01)

(52) U.S. Cl.
CPC ............... *A42B 3/14* (2013.01); *A61N 5/067* (2021.08); *A61N 2005/0647* (2013.01)

(58) Field of Classification Search
CPC .... A42B 3/14; A61N 5/067; A61N 2005/065; A61N 2005/0651; A61N 2005/0652; A61N 2005/0653; A61N 2005/0654; A61N 2005/0655; A61N 2005/0647; A61N 2005/0645
USPC .......................................................... 607/89
See application file for complete search history.

(56) References Cited

U.S. PATENT DOCUMENTS

| | | | | |
|---|---|---|---|---|
| 2,639,428 A | * | 5/1953 | MacLean | A42B 3/14 2/416 |
| 2,735,099 A | * | 2/1956 | Lewis | A42B 3/14 2/416 |
| 5,323,493 A | * | 6/1994 | Ogiba | G02C 3/02 2/10 |
| 2007/0000031 A1 | * | 1/2007 | Makris | A42B 3/0433 2/411 |
| 2011/0022132 A1 | * | 1/2011 | Kim | A61H 7/006 607/91 |
| 2011/0092863 A1 | | 4/2011 | Kim et al. | |
| 2015/0375007 A1 | * | 12/2015 | Takeuchi | A61N 5/0617 607/90 |
| 2018/0008839 A1 | | 1/2018 | Hamid | |
| 2019/0201713 A1 | | 7/2019 | Segal | |

* cited by examiner

*Primary Examiner* — Aaron F Roane
(74) *Attorney, Agent, or Firm* — Rumit Ranjit Kanakia

(57) ABSTRACT

The present disclosure discloses an intelligent hair growth helmet, and relates to the field of medical instruments. The intelligent hair growth helmet includes a helmet outer shell; an inner housing is fixedly mounted in the helmet outer shell; a plurality of supporting pipes are uniformly and fixedly mounted on the inner housing; U-shaped supporting plates are fixedly mounted on inner walls of two sides of the inner housing; a plurality of mounting holes are formed in the two U-shaped supporting plates; the same cushion block is slidably sleeved in two mounting holes on the same side; two mounting shafts are symmetrically and fixedly mounted on the cushion block.

10 Claims, 4 Drawing Sheets

INTELLIGENT HAIR GROWTH HELMET

TECHNICAL FIELD

The present disclosure relates to the technical field of medical instruments, and in particular, an intelligent hair growth helmet.

BACKGROUND

In laser hair growth, a low-energy laser with a wavelength of 650 nm, and a light-emitting diode (LED) red light are mainly used. It has been medically proven that the laser hair growth can stimulate the growth of basic energy ATP of human cells. Laser can penetrate the scalp by 3 to 5 mm and directly reach the roots of hair follicles, thus generating the cell growth ability, enhancing the hair follicle metabolism, improving the hair follicle cell proliferation ability, improving the hair follicle growth ability, resisting invasion of DHT to the hair follicles, and causing thicker hairs to grow in an alopecia area.

In the existing art, the hair growth helmet has a poor effect, so an intelligent hair growth helmet is needed to meet people's needs.

SUMMARY

The present disclosure aims to provide an intelligent hair growth helmet, so as to solve the problem of low performance of the hair growth helmet mentioned in the background art.

In order to achieve the above-mentioned objective, the present disclosure provides the following technical solution: An intelligent hair growth helmet includes a helmet outer shell; an inner housing is fixedly mounted in the helmet outer shell; the helmet outer shell is used to protect the inner housing; the inner housing is used to facilitate a user to wear the helmet; a plurality of supporting pipes are uniformly and fixedly mounted on the inner housing; the supporting pipes are used to guarantee the connection between the helmet outer shell and the inner housing and also dilate the helmet outer shell and the inner housing; U-shaped supporting plates are fixedly mounted on inner walls of two sides of the inner housing; a plurality of mounting holes are formed in the two U-shaped supporting plates; the same cushion block is slidably sleeved in two mounting holes on the same side; two mounting shafts are symmetrically and fixedly mounted on the cushion block and are fixedly sleeved in the two mounting holes, respectively.

By adopting a total of 114 pieces of LD+LED independent light source irradiation points, a coverage area is large; it is more comprehensive and effective for treatment of different scalps; blue light with a wavelength of 470 nm is added, which can achieve a sterilization and inflammation diminishing effect and synchronously suppress the secretion of glandular integumentaria and promote tissues to be restored; a small fan is added, which can dissipate internal heat by means of accelerating air convection, and a user feels more comfortable during use; and by a multifunctional interface, the user can use a mobile power supply to charge a product or directly use the mobile power supply to drive the product, and it is used more conveniently and flexibly.

Preferably, a supporting block is fixedly mounted on the cushion block; a mounting slot is formed in the supporting block; the cushion block is slidably sleeved in the mounting slot; the cushion block is used to fix the supporting block on the U-shaped supporting plate.

Preferably, two fixed rotating shafts are symmetrically and fixedly sleeved on the helmet outer shell; the two fixed rotating shafts are fixedly mounted on a connection box; and the connection box and the fixed rotating shafts cooperate with each other to ensure the fixing stability of the U-shaped supporting plates.

Preferably, the connection box is fixedly provided with a fixed rotating shaft. The connection box and the fixed rotating shaft cooperate with each other to ensure the fixing stability of the U-shaped supporting plates.

Preferably, an internal connection block is fixed on the U-shaped supporting plates; the fixed rotating shafts are fixedly mounted on the internal connection block; and the internal connection block cooperates with the fixed rotating shafts to fix the U-shaped supporting plates on an inner wall of the inner housing.

Preferably, air holes are formed in the helmet outer shell. The air holes are used to ensure the air permeability of the helmet, so that a user feels more comfortable during use.

Preferably, two rotating shaft holes are symmetrically formed in the helmet outer shell. The rotating shaft holes are used to facilitate the fixing and the mounting of the fixed rotating shafts.

Preferably, the inner wall of the helmet outer shell is fixedly provided with a connection block. The connection block is used to ensure the supporting stability of the helmet outer shell.

Preferably, the inner housing is fixedly provided with a laser generator; a through hole is formed in the laser generator; the laser generator is used to emit laser; and the blue light with the wavelength of 470 nm can achieve the sterilization and inflammation diminishing effect and synchronously suppress the secretion of glandular integumentaria and promote tissues to be restored, thus ensuring the hair growth effect of the helmet.

Preferably, a threaded hole is formed in the inner housing, and sliding holes are symmetrically formed in an inner wall of the inner housing. The threaded hole and the connection block cooperate with each other to ensure fixing between the helmet outer shell and the inner housing.

The present disclosure has the beneficial effects:

In the present disclosure, by means of the arrangement of the laser generator and other structures, the laser generator can emit the blue light with the wavelength of 470 nm, and blue light with the wavelength of 470 nm can achieve the sterilization and inflammation diminishing effect and synchronously suppress the secretion of glandular integumentaria and promote tissues to be restored, thus ensuring the hair growth effect of the helmet.

In the present disclosure, the helmet outer shell is used to protect the inner housing; the inner housing is used to facilitate the user to wear the helmet; the supporting pipes are used to ensure the connection between the helmet outer shell and the inner housing and also dilate them; and the U-shaped supporting plates are used to ensure the mounting stability of the supporting blocks.

In the present disclosure, by adopting a total of 114 pieces of LD+LED independent light source irradiation points, the coverage area is large; it is more comprehensive and effective for treatment of different scalps.

In the present disclosure, the blue light with the wavelength of 470 nm is added, which can achieve the sterilization and inflammation diminishing effect and synchronously suppress the secretion of glandular integumentaria and promote tissues to be restored.

In the present disclosure, the small fan is added, which can dissipate internal heat by means of accelerating air convection, and the user feels more comfortable during use.

In the present disclosure, by additionally providing the multifunctional interface, the user can use the mobile power supply to charge a product or directly use the mobile power supply to drive the product, and it is used more conveniently and flexibly.

Figure 1:
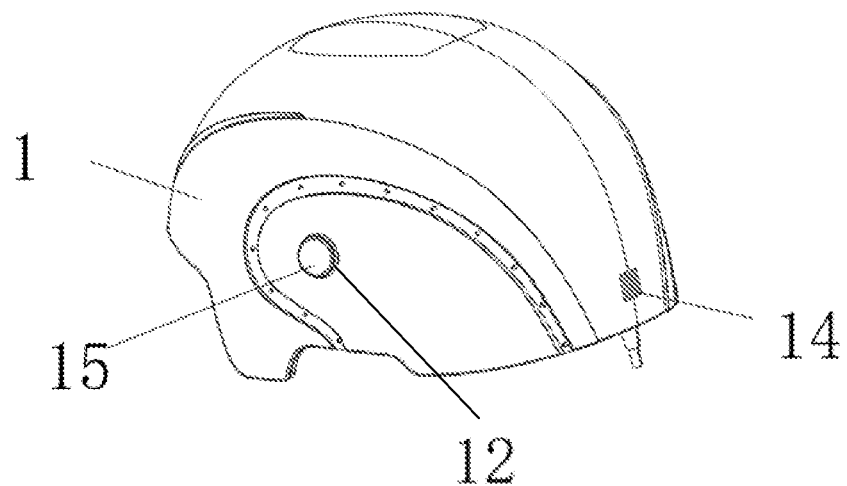
FIG. 1 is a schematic diagram of a top structure of an intelligent hair growth helmet provided by the present disclosure.

In the drawings: 1: helmet outer shell; 2: inner housing; 3: supporting pipe; 4: U-shaped supporting plate; 5: internal connection block; 6: supporting block; 7: mounting slot; 8: cushion block; 9: mounting shaft; 10: connection box; 11: mounting hole; 12: rotating shaft hole; 13: connection block; 14: air hole; 15: fixed rotating shaft; 16: threaded hole; 17: through hole; 18: sliding hole; 19: laser generator.

DETAILED DESCRIPTION OF THE EMBODIMENTS

The following clearly and completely describes the technical solution in the embodiments of the present disclosure in combination with the accompanying drawings of the embodiments of the present disclosure. Apparently, the described embodiments are only part of the embodiments of the present disclosure, not all embodiments.

Figure 2:
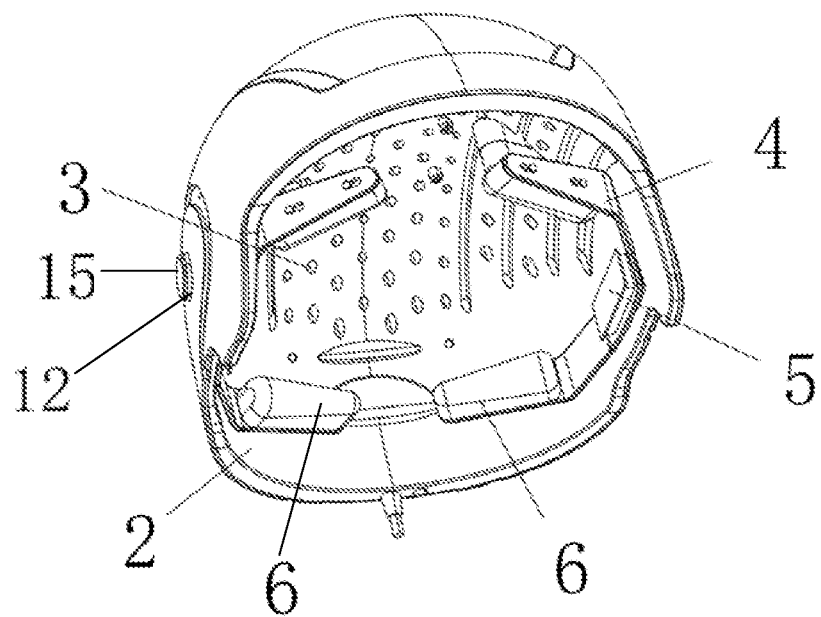
FIG. 2 is a schematic diagram of a bottom structure of an intelligent hair growth helmet provided by the present disclosure.
Figure 6:
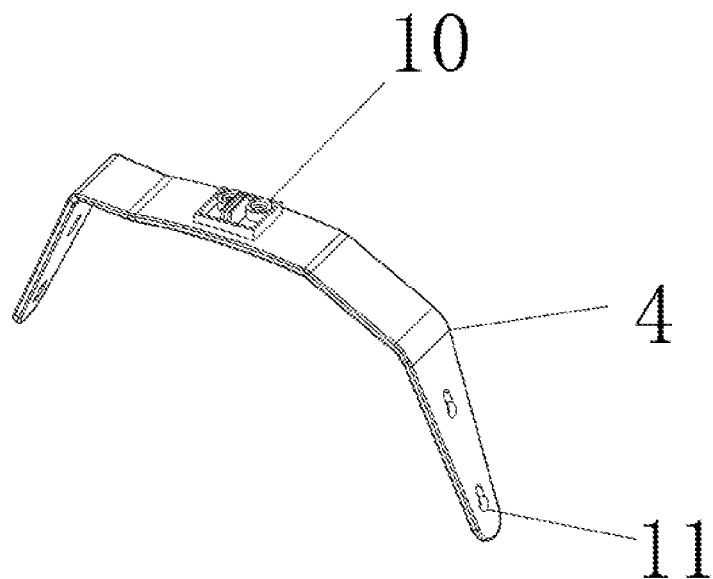
FIG. 6 is a schematic structural diagram of a U-shaped supporting plate of an intelligent hair growth helmet provided by the present disclosure.
Figure 7:
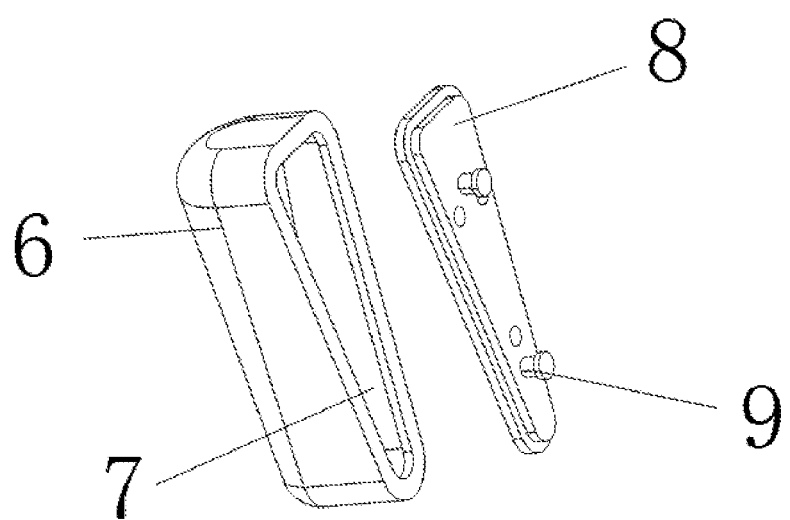
FIG. 7 is a schematic structural diagram of connection of a cushion block and other structures in an inner housing of an intelligent hair growth helmet provided by the present disclosure.

Referring to FIGS. 1 and 2, an intelligent hair growth helmet includes a helmet outer shell 1; an inner housing 2 is fixedly mounted in the helmet outer shell 1; the helmet outer shell 1 is used to protect the inner housing 2; the inner housing 2 is used to facilitate a user to wear the helmet; a plurality of supporting pipes 3 are uniformly and fixedly mounted on the inner housing 2; the supporting pipes 3 are used to guarantee the connection between the helmet outer shell 1 and the inner housing 2 and also dilate them; two U-shaped supporting plates 4 are fixedly mounted on inner walls of two sides of the inner housing 2 respectively; referring to FIGS. 6 and 7, two mounting holes 11 are formed in each of the two U-shaped supporting plates 4; a cushion block 8 is slidably connected in the two mounting holes 11 of each of the two U-shaped supporting plates 4; two mounting shafts 9 are symmetrically and fixedly mounted on each cushion block 8 and are fixedly sleeved in the two mounting holes 11, respectively.

By adopting a total of 114 pieces of LD+LED independent light source irradiation points, a coverage area is large; it is more comprehensive and effective for treatment of different scalps; blue light with a wavelength of 470 nm is added, which can achieve a sterilization and inflammation diminishing effect and synchronously suppress the secretion of glandular integumentaria and promote tissues to be restored; a small fan is added, which can dissipate internal heat by means of accelerating air convection, and a user feels more comfortable during use; and by a multifunctional interface, the user can use a mobile power supply to charge a product or directly use the mobile power supply to drive the product, and it is used more conveniently and flexibly.

In the present disclosure, referring to FIGS. 6 and 7, a supporting block 6 is fixedly mounted on the cushion block 8; a mounting slot 7 is formed in the supporting block 6; the cushion block 8 is slidably sleeved in the mounting slot 7; and the cushion block 8 is used to fix the supporting block 6 on the U-shaped supporting plate 4.

In the present disclosure, referring to FIGS. 2 and 6, two fixed rotating shafts 15 are symmetrically and fixedly sleeved on the helmet outer shell 1; each of the two fixed rotating shafts 15 is fixedly mounted on a connection box 10 of a corresponding one of the two U-shaped supporting plates 4; and the connection boxes 10 and the fixed rotating shafts 15 cooperate with each other to ensure fixing stability of the U-shaped supporting plates 4.

In the present disclosure, referring to FIGS. 1-2 and 6, each of the connection boxes 10 is fixedly connected with a corresponding one of the fixed rotating shafts 15. The connection boxes 10 and the fixed rotating shafts 15 cooperate with each other to ensure the fixing stability of the U-shaped supporting plates 4.

In the present disclosure, referring to FIGS. 1 and 2, an internal connection block 5 is fixed on each of the U-shaped supporting plates 4; each of the fixed rotating shafts 15 is fixedly mounted on corresponding one of the internal connection blocks 5 through corresponding one of the U-shaped supporting plates 4; and the internal blocks 5 cooperates with the fixed rotating shafts 15 to fix the U-shaped supporting plates 4 on an inner wall of the inner housing 2.

Figure 3:
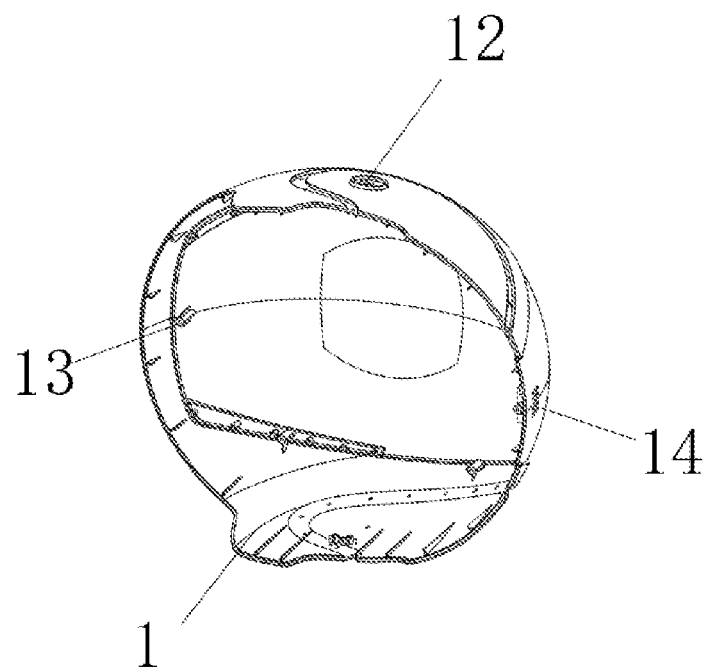
FIG. 3 is a schematic structural diagram of a helmet outer shell of an intelligent hair growth helmet provided by the present disclosure.

In the present disclosure, referring to FIGS. 1 and 3, air holes 14 are formed in the helmet outer shell 1. The air holes 14 are used to ensure the air permeability of the helmet, so that a user feels more comfortable during use.

In the present disclosure, referring to FIGS. 1-3, two rotating shaft holes 12 are symmetrically formed in the helmet outer shell 1. The rotating shaft holes 12 are used to facilitate the fixing and the mounting of the fixed rotating shafts 15.

In the present disclosure, referring to FIG. 3, the inner wall of the helmet outer shell 1 is fixedly provided with a connection block 13. The connection block 13 is used to ensure the supporting stability of the helmet outer shell 1.

Figure 4:
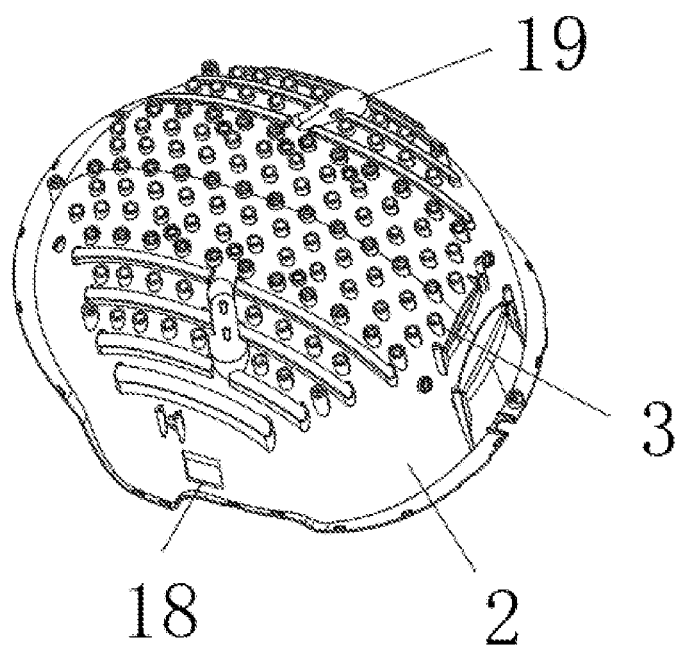
FIG. 4 is a schematic structural diagram of an exterior view of an inner housing of an intelligent hair growth helmet provided by the present disclosure.
Figure 5:
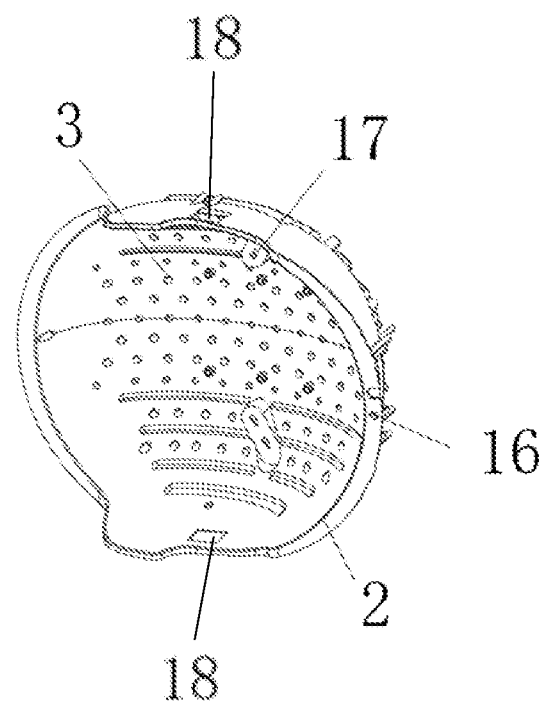
FIG. 5 is a schematic structural diagram of an interior view of an inner housing of an intelligent hair growth helmet provided by the present disclosure.

In the present disclosure, referring to FIGS. 4-5, the inner housing 2 is fixedly provided with a laser generator 19; a through hole 17 is formed in the laser generator 19; the laser generator 19 is used to emit laser; and the blue light with a wavelength of 470 nm can achieve sterilization and inflammation diminishing effect and synchronously suppress the secretion of glandular integumentaria and promote tissues to be restored, thus ensuring the hair growth effect of the helmet.

In the present disclosure, referring to FIGS. 3-5, a threaded hole 16 is formed in the inner housing 2, and two sliding holes 18 are symmetrically formed in an inner wall of the inner housing 2. The threaded hole 16 and the connection block 13 cooperate with each other to ensure fixing between the helmet outer shell 1 and the inner housing 2.

The working principle of the present disclosure is as follows:

The helmet outer shell 1 is used to protect the inner housing 2; the inner housing 2 is used to facilitate the user to wear the helmet; the supporting pipes 3 are used to ensure the connection between the helmet outer shell 1 and the inner housing 2 and also dilate them; the U-shaped supporting plates 4 are used to ensure the mounting stability of the supporting blocks 6; the cushion blocks 8 are used to fix the supporting blocks 6 on the U-shaped supporting plates 4; the cooperation between the mounting holes 11 and the mounting shafts 9 completes the fixing between the cushion blocks 8 and the supporting blocks 6; the cooperation between the connection boxes 10 and the fixed rotating shafts 15 ensures the fixing stability of the U-shaped supporting plates 4; the rotating shaft holes 12 are used to facilitate the fixing and the mounting of the fixed rotating shafts 15; the air holes 14 are used for air permeation; the cooperation between the connection block 13 and the threaded hole 16 ensures the fixing between the helmet outer shell 1 and the inner housing 2; the sliding holes 18 are used to fix the connection box 10; and the laser generator 19 is used to generate laser.

In the present disclosure, by adopting a total of 114 pieces of LD+LED independent light source irradiation points, the whole machine has a large coverage area and is more comprehensive and effective for treatment of different scalps.

In the present disclosure, the laser generator 19 is used to output blue light. The blue light with the wavelength of 470 nm can achieve the sterilization and inflammation diminishing effect and synchronously suppress the secretion of glandular integumentaria and promote tissues to be restored.

In the present disclosure, the small fan is added, which can dissipate internal heat by means of accelerating air convection, and the user feels more comfortable during use.

In the present disclosure, by additionally providing the multifunctional interface, the user can use the mobile power supply to charge a product or directly use the mobile power supply to drive the product, and it is used more conveniently and flexibly.

The above descriptions are only specific preferred implementation modes of the present disclosure, but the scope of protection of the present disclosure is not limited thereto. For any person skilled in the art, within the technical scope disclosed by the present disclosure, equivalent substitutions or changes made according to the technical solution of the present disclosure and an inventive idea of the present disclosure shall all fall within the scope of protection of the present disclosure.

What is claimed is:

1. An intelligent hair growth helmet, comprising a helmet outer shell (1), wherein an inner housing (2) is fixedly mounted in the helmet outer shell (1); a plurality of supporting pipes (3) are uniformly and fixedly mounted on the inner housing (2); two U-shaped supporting plates (4) are fixedly mounted on inner walls of two sides of the inner housing (2) respectively; two mounting holes (11) are formed in each of the two U-shaped supporting plates (4); a cushion block (8) is slidably connected in two mounting holes (11) of each of the two U-shaped supporting plates (4); two mounting shafts (9) are symmetrically and fixedly mounted on each cushion block (8) and are fixedly sleeved in the two mounting holes (11) of corresponding one of the two U-shaped supporting plates, respectively.

2. The intelligent hair growth helmet according to claim 1, wherein a supporting block (6) is fixedly mounted on each cushion block (8); a mounting slot (7) is formed in each supporting block (6); and the cushion block (8) is slidably sleeved in the mounting slot (7).

3. The intelligent hair growth helmet according to claim 1, wherein a connection box (10) is fixedly mounted on each of the two U-shaped supporting plates (4).

4. The intelligent hair growth helmet according to claim 1, wherein two fixed rotating shafts (15) are symmetrically and fixedly sleeved on the helmet outer shell (1); and each of the two fixed rotating shafts (15) is fixedly mounted on the connection box (10) on corresponding one of the two U-shaped supporting plates.

5. The intelligent hair growth helmet according to claim 1, wherein an internal connection block (5) is fixed on each of the two U-shaped supporting plates (4); and each of the fixed rotating shafts (15) is fixedly mounted on the internal connection block (5) through corresponding one of the two U-shaped supporting plates.

6. The intelligent hair growth helmet according to claim 1, wherein air holes (14) are formed in the helmet outer shell (1).

7. The intelligent hair growth helmet according to claim 1, wherein two rotating shaft holes (12) are symmetrically formed in the helmet outer shell (1) and configured to facilitate fixing and mounting of the fixed rotating shafts (15).

8. The intelligent hair growth helmet according to claim 1, wherein a connection block (13) is fixedly mounted on an inner wall of the helmet outer shell (1), and a threaded hole (16) is formed in the inner housing (2) and configured to cooperate with the connection block (13) to ensure a connection between the helmet outer shell (1) and the inner housing (2).

9. The intelligent hair growth helmet according to claim 1, wherein a laser generator (19) is fixedly mounted on the inner housing (2); and a through hole (17) is formed in the laser generator (19).

10. The intelligent hair growth helmet according to claim 3, wherein two sliding holes (18) are symmetrically formed in an inner wall of the inner housing (2) corresponding to the connection boxes (10) on the two U-shaped supporting plates.

* * * * *